(12) United States Patent
Chou et al.

(10) Patent No.: US 8,610,889 B2
(45) Date of Patent: Dec. 17, 2013

(54) AUTOMATED OPTICAL INSPECTION DEVICE AND CALIBRATION METHOD THEREOF

(75) Inventors: Ping-hung Chou, Guangdong (CN); Chengming He, Guangdong (CN)

(73) Assignee: Shenzhen China Star Optoelectronics Technology Co., Ltd., Guangdong (CN)

( * ) Notice: Subject to any disclaimer, the term of this patent is extended or adjusted under 35 U.S.C. 154(b) by 117 days.

(21) Appl. No.: 13/127,738

(22) PCT Filed: Mar. 10, 2011

(86) PCT No.: PCT/CN2011/071704
§ 371 (c)(1),
(2), (4) Date: May 5, 2011

(87) PCT Pub. No.: WO2012/113165
PCT Pub. Date: Aug. 30, 2012

(65) Prior Publication Data
US 2012/0268732 A1    Oct. 25, 2012

(30) Foreign Application Priority Data
Feb. 25, 2011    (CN) .......................... 2011 1 0046752

(51) Int. Cl.
*G01N 21/00*    (2006.01)
(52) U.S. Cl.
USPC ...................................................... 356/237.1

(58) Field of Classification Search
None
See application file for complete search history.

(56) References Cited

U.S. PATENT DOCUMENTS

2003/0223072 A1    12/2003  Schulz
2005/0111004 A1    5/2005   Kim et al.

FOREIGN PATENT DOCUMENTS

| CN | 1407329 A | 4/2003 |
|---|---|---|
| CN | 1908638 A | 2/2007 |
| EP | 1477797 A1 | 11/2004 |
| JP | 2004184242 A | 7/2004 |

*Primary Examiner* — Gregory J Toatley
*Assistant Examiner* — Amanda Merlino
(74) *Attorney, Agent, or Firm* — Mark M. Friedman

(57) ABSTRACT

The present invention discloses an automated optical inspection device and a calibration method thereof. The automated optical inspection device has a machine table and a camera. The machine table has a first fixing base for placing a product plate and a second fixing base for placing a standard plate, and the second fixing base is disposed above the first fixing base. The camera is disposed above the machine table and is used to move upward a predetermined distance at a predetermined time and then scan the standard plate on the second fixing base to achieve calibration. The present invention automates the calibration process for the automated optical inspection device, so as to reduce overall work time.

14 Claims, 4 Drawing Sheets

AUTOMATED OPTICAL INSPECTION DEVICE AND CALIBRATION METHOD THEREOF

FIELD OF THE INVENTION

The present invention relates to an automated optical inspection device, especially to an automated optical inspection device and a calibration method thereof that reduces the work time for the overall process.

BACKGROUND OF THE INVENTION

In a manufacturing process of liquid crystal panel, an automated optical inspection device is generally used to inspect the glass substrates of the liquid crystal panel. The automated optical inspection device mainly uses an optical device to capture surface images of the glass substrates and detects flaws like impurities or abnormal patterns.

With reference to FIG. 1, FIG. 1 is a flow chart of daily calibration executed by a conventional automated optical inspection device. When executing daily calibration, the automated optical inspection device firstly clear products waiting to be inspected (S900). Then the device operators manually set a standard plate for calibration directly into the automated optical inspection device (S901) or set the standard plate via a plate holder into the automated optical inspection device (S902), so as to execute daily calibration. After completing calibration (S903), the automated optical inspection device then restarts to receive products to continue inspecting (S904).

The means of manually setting the standard plate by operators may likely damage the standard plate. Once the standard plate is damaged, it will have to be reproduced. Besides, the calibration process disclosed in FIG. 1 has to remove all the products waiting to be inspected inside the automated optical device in advance, so that the standard plate can be set to execute calibration, and it is to be noted that such means is time-consuming.

Hence, it is necessary to provide an automated optical inspection device and a calibration method thereof to overcome the problems existing in the conventional technology.

SUMMARY OF THE INVENTION

A primary object of the invention is to provide an automated optical inspection device that prevents steps of manually set in and draw out the standard plate, so as to reduce the work time of the overall process and enhance product inspection efficiency.

A secondary object of the present invention is to provide a calibration method of an automated optical inspection device that is executed by the aforementioned automated optical inspection device, wherein the daily calibration process is automated for reducing calibration time, so as to enhance product inspection efficiency.

To achieve the above object, the present invention provides an automated optical inspection device, and the automated optical inspection device comprises:

a machine table having a first fixing base for placing a product plate and a second fixing base for placing a standard plate, wherein the second fixing base is disposed above the first fixing base; and a first camera disposed above the machine table and used to move upward a predetermined distance at a predetermined time and then scan the standard plate on the second fixing base to achieve calibration.

In one embodiment of the present invention, the first camera moves downward the predetermined distance after calibration and scans the product plate on the first fixing base.

In one embodiment of the present invention, the second fixing base moves relative to the first fixing base.

In one embodiment of the present invention, further comprises a light source device disposed above the machine table beside the first camera and used to provide illumination for the first fixing base and the second fixing base.

In one embodiment of the present invention, further comprises a second camera disposed under the machine table and is used to scan the product plate on the first fixing base synchronously with the first camera.

In one embodiment of the present invention, the light source device is an illumination-angle adjustable light source device.

The present invention further provides a calibration method of an automated optical inspection device, and the calibration method is executed by the automated optical inspection device, wherein the automated optical device comprises a machine table and a first camera, and the machine table has a first fixing base for placing a product plate and a second fixing base for placing a standard plate, and the second fixing base is disposed above the first fixing base; the first camera is disposed above the machine table; the calibration method of the automated optical inspection device comprises steps of:

the first camera moves upward a predetermined distance at a predetermined time and then scan the standard plate on the second fixing base to achieve calibration.

In one embodiment of the present invention, the first camera moves downward the predetermined distance after calibration and continues to scan the product plate on the first fixing base.

In one embodiment of the present invention, the automated optical inspection device further comprises a light source device disposed above the machine table beside the first camera and used to provide illumination for the first fixing base and the second fixing base.

In one embodiment of the present invention, the automated optical inspection device further comprises a second camera disposed under the machine table, wherein the second camera scans the product plate on the first fixing base synchronously with the first camera.

The present invention sets a fixing base inside a machine table for placing a standard plate over a long period of time and operates with an automated calibration process, so as to prevent actions of repeatedly setting in and drawing out the standard plate and avoid damage risks caused by operators that manually move the standard plate, and further reduce the work time of overall process to enhance product inspection efficiency.

DETAILED DESCRIPTION OF THE PREFERRED EMBODIMENTS

The foregoing objects, features and advantages adopted by the present invention can be best understood by referring to the following detailed description of the preferred embodiments and the accompanying drawings. Furthermore, the directional terms described in the present invention, such as upper, lower, front, rear, left, right, inner, outer, side and etc., are only directions referring to the accompanying drawings, so that the used directional terms are used to describe and understand the present invention, but the present invention is not limited thereto.

Generally, before executing a calibration process for automated optical inspection, it is necessary to stop running the product line to stop putting in new product plates and remove the product plates waiting to be inspected, so that a standard plate can be set in for executing the daily calibration process. Therefore, the present invention is to mount a fixing base inside the automated optical inspection device for placing at least one standard plate to prevent complicated steps of clearing product plates and sending in the standard plate.

Figure 2:
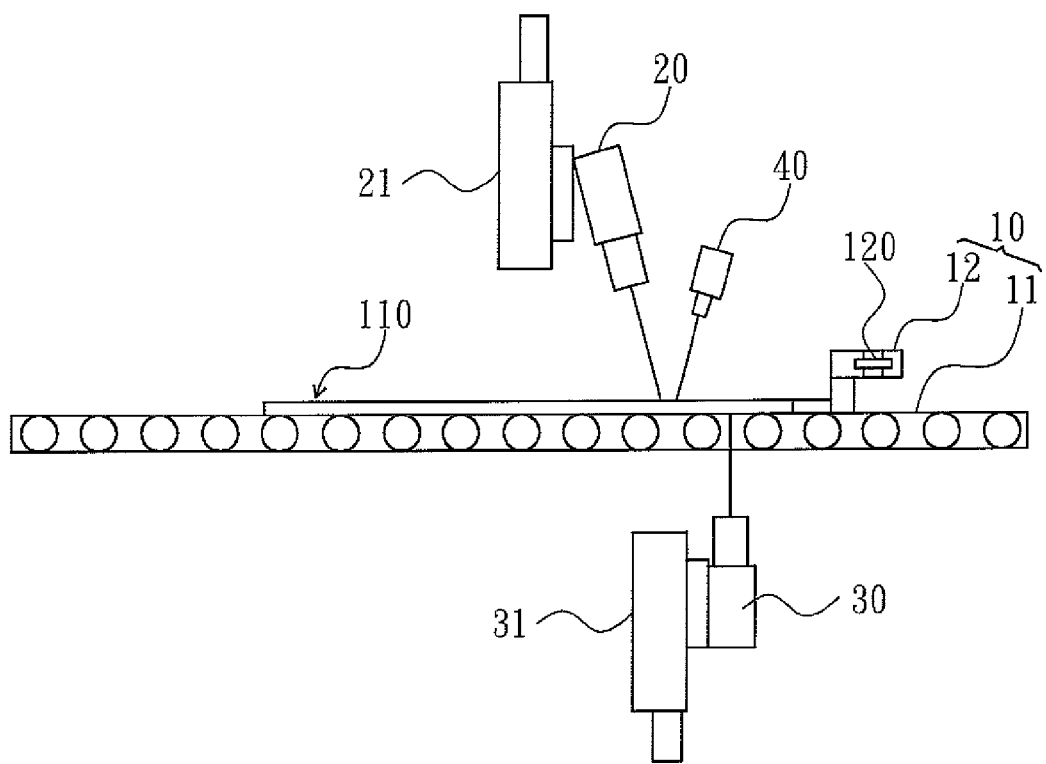
FIG. 2 is a side view of an automated optical inspection device of a preferred embodiment in accordance with the present invention.

With reference to FIG. 2, FIG. 2 is a side view of an automated optical inspection device of a preferred embodiment in accordance with the present invention. The optical inspection device mainly comprises a machine table 10 and a first camera 20. The machine table 10 has a first fixing base 11 and a second fixing base 12. The first fixing base 11 is used for placing at least one product plate 110. The second fixing base 12 is disposed above one end of the first fixing base 11 and is used for placing at least one standard plate 120. The second fixing base 12 can move relative to the first fixing base 11. The second fixing base 12 may be mounted over a top of the first fixing base 11, so as not to affect operation of product line.

With reference to FIG. 2, the first camera 20 is disposed above the machine table 10, and may be mounted on a first control base 21. The movement of the first camera 20 is controlled by the first control base 21.

Figure 3:
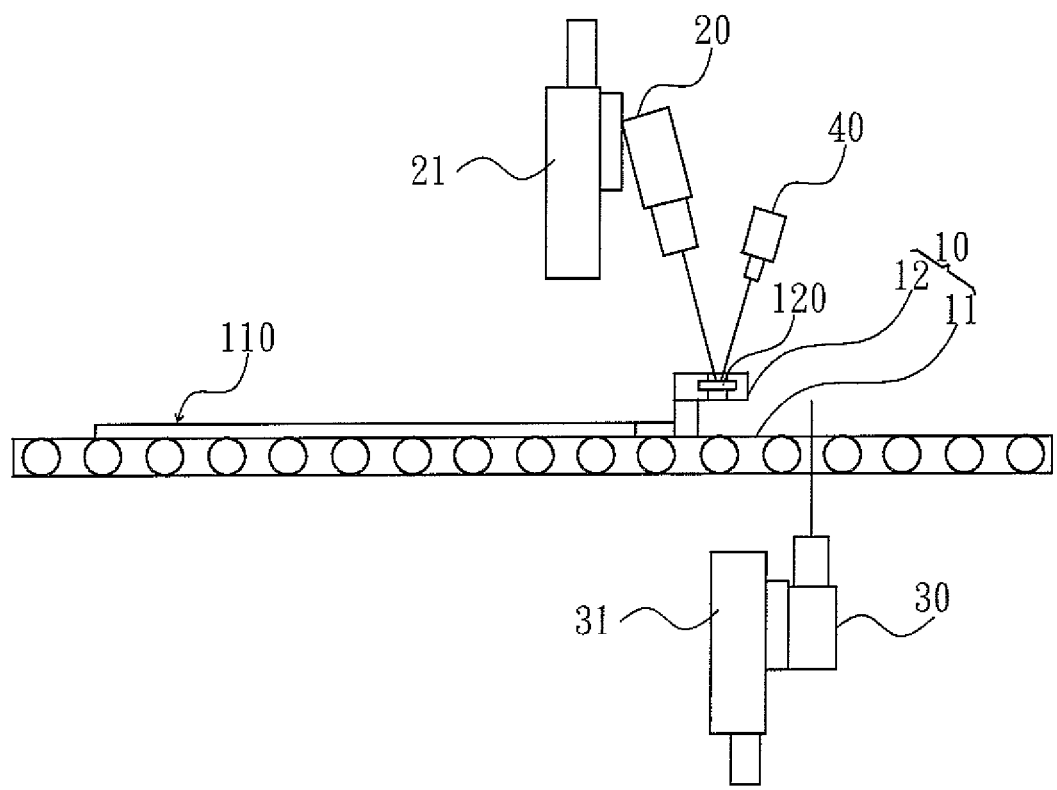
FIG. 3 is a side view of the automated optical inspection device in FIG. 2 when starting calibration function.

With further reference to FIG. 3, when the machine table works at a predetermined time for daily calibration, the product line will automatically pause to stop sending in product plates. Since the second fixing base 12 is disposed above one end of the first fixing base 11, the first camera 20 will first move upward a predetermined distance to focus on the standard plate 120 on the second fixing base 12 and scan the standard plate 120, and then transmit scanning data to a corresponding control system to achieve calibration, wherein the first camera 20 moves from one end of the standard plate 120 to another end during scanning. The first camera 20 then moves downward the predetermined distance to focus on the product plate 110 on the first fixing base after the calibration and scans the product plate 110. The first camera 20 moves from one end of the product plate 110 to another end during scanning.

Figure 1:
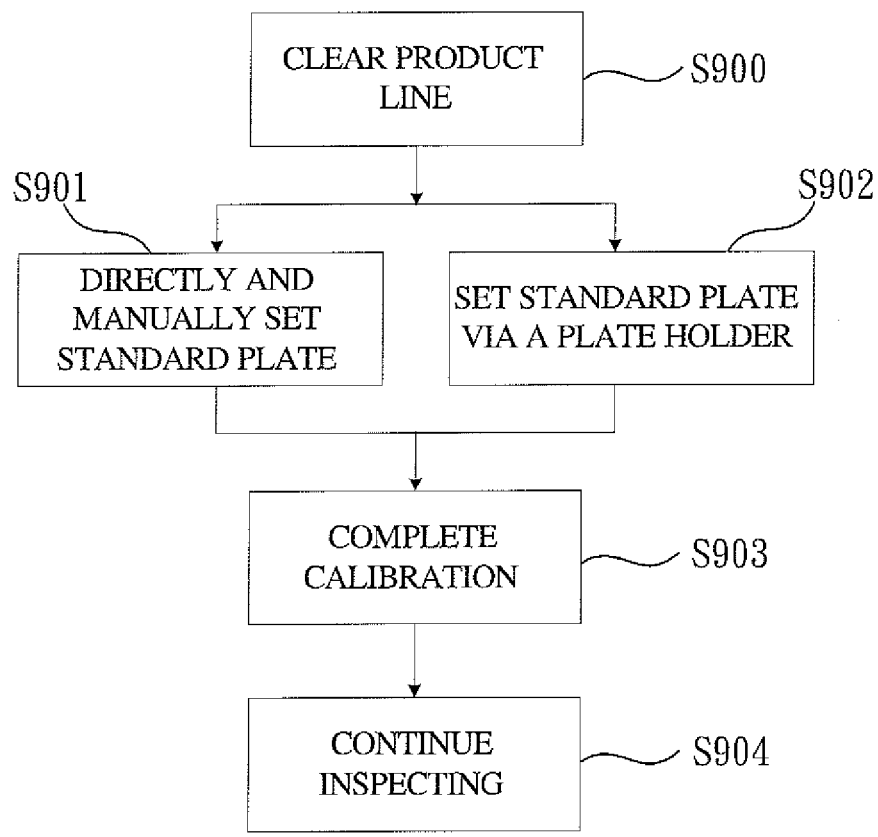
FIG. 1 is a flow chart of an automated optical inspection device executing daily calibration according to a prior art.

With reference to FIGS. 1 and 3, the automated optical inspection device of the present invention further comprises a second camera 30. The second camera 30 is disposed under the machine table 10, and may be mounted on the second control base 31. The movement of the first camera 20 is controlled by the first control base 21. The second camera 30 scans the product plate 110 on the first fixing base 11 synchronously with the first camera 20.

With reference to FIGS. 1 and 3, the automated optical inspection device of the present invention further comprises a light source device 40. The light source device 40 is disposed above the machine table 10 beside the first camera 20 and is to provide illumination for the first fixing base 11 and the second fixing base 12, such that the first camera 20 can capture clear images from the product plate 110 and the standard plate 120. The light source device 40 is preferably an illumination-angle adjustable light source device.

Figure 4:
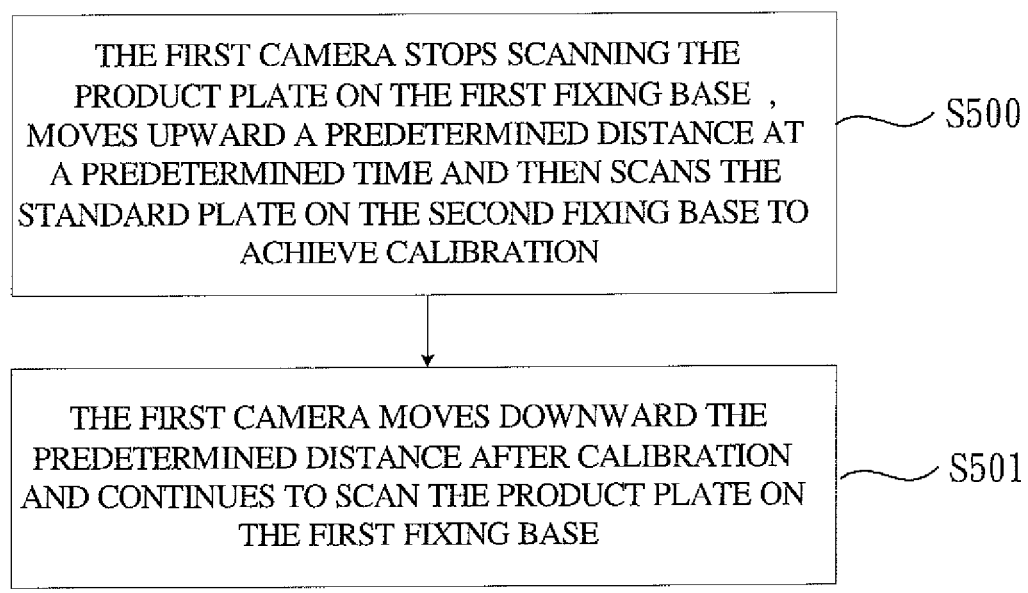
FIG. 4 is a flow chart of a calibration method of the automated optical inspection device in accordance with the present invention.

With reference to FIG. 4, FIG. 4 is a flow chart of a calibration method of the automated optical inspection device in accordance with the present invention. The calibration method is executed by the aforementioned automated optical device. The calibration method of the automated optical inspection device comprises steps of:

Step S500: the first camera stops scanning the product plate on the first fixing base, moves upward a predetermined distance at a predetermined time and then scans the standard plate on the second fixing base to achieve calibration;

For example, every day at 8 A.M., the product line automatically stops running, and the first camera stops scanning product plates and moves upward a predetermined distance to focus and scan the standard plate and then transmit scanning data of the standard plate to a control system to achieve the calibration of AOI device.

Step S501: the first camera moves downward the predetermined distance after calibration and continues to scan the product plate on the first fixing base.

The automated optical inspection device operates with the calibration method can timely executes calibration. And after the calibration, the first camera moves downward the predetermined distance to focus on the product plate and the product line continues.

In summary, comparing with the means of manually moving standard plate by operators that easily damages the standard plate and the calibration is time-consuming, the present invention setting a second fixing base in the machine table for placing a standard plate over a long period of time, and operates with the automated calibration process, so as to prevent damage risks caused by manually moving the standard plate by operators and substantially reduce the time cost for daily calibration, and further enhance the efficiency of inspecting products to help increasing the capacity of production.

The present invention has been described with a preferred embodiment thereof and it is understood that many changes and modifications to the described embodiment can be carried out without departing from the scope and the spirit of the invention that is intended to be limited only by the appended claims.

The invention claimed is:

1. An automated optical inspection device, characterized in that: the automated optical inspection device comprises:
   a machine table having a first fixing base for placing a product plate and a second fixing base for placing a standard plate, wherein the second fixing base is disposed above the first fixing base;
   a first camera disposed above the machine table and used to move upward a predetermined distance at a predetermined time and then scan the standard plate on the second fixing base to achieve calibration, wherein the first camera moves downward the predetermined distance after calibration and then scans the product plate on the first fixing base; and
   a light source device disposed above the machine table beside the first camera and to provide illumination for the first fixing base and the second fixing base.

2. The automated optical inspection device as claimed in claim 1, characterized in that: the second fixing base moves relative to the first fixing base.

3. The automated optical inspection device as claimed in claim 1, characterized in that: the automated optical inspection device further comprises a second camera disposed under the machine table, and the second camera scans the product plate on the first fixing base synchronously with the first camera.

4. The automated optical inspection device as claimed in claim 1, characterized in that: the light source device is an illumination-angle adjustable light source device.

5. An automated optical inspection device, characterized in that: the automated optical inspection device comprises:
- a machine table having a first fixing base for placing a product plate and a second fixing base for placing a standard plate, wherein the second fixing base is disposed above the first fixing base; and
- a first camera disposed above the machine table and used to move upward a predetermined distance at a predetermined time and then scan the standard plate on the second fixing base to achieve calibration.

6. The automated optical inspection device as claimed in claim 5, characterized in that: the first camera moves downward the predetermined distance after calibration and scans the product plate on the first fixing base.

7. The automated optical inspection device as claimed in claim 5, characterized in that: the second fixing base moves relative to the first fixing base.

8. The automated optical inspection device as claimed in claim 5, characterized in that: the automated optical inspection device further comprises a light source device disposed above the machine table beside the first camera and used to provide illumination for the first fixing base and the second fixing base.

9. The automated optical inspection device as claimed in claim 6, characterized in that: the automated optical inspection device further comprises a second camera disposed under the machine table and is used to scan the product plate on the first fixing base synchronously with the first camera.

10. The automated optical inspection device as claimed in claim 8, characterized in that: the light source device is an illumination-angle adjustable light source device.

11. A calibration method of an automated optical inspection device, characterized in that: the calibration method of an automated optical inspection device is executed by an automated optical inspection device, wherein the automated optical inspection device has a machine table and a first camera, and the machine table has a first fixing base for placing a product plate and a second fixing base for placing a standard plate, and the second fixing base is disposed above the first fixing base; the first camera is disposed above the machine table; the calibration method of the automated optical inspection device comprises steps of:
- the first camera moves upward a predetermined distance at a predetermined time and then scan the standard plate on the second fixing base to achieve calibration.

12. The automated optical inspection device as claimed in claim 11, characterized in that: the first camera moves downward the predetermined distance after calibration and continues to scan the product plate on the first fixing base.

13. The automated optical inspection device as claimed in claim 11, characterized in that: the automated optical inspection device further comprises a light source device disposed above the machine table beside the first camera and used to provide illumination for the first fixing base and the second fixing base.

14. The automated optical inspection device as claimed in claim 12, characterized in that: the automated optical inspection device further comprises a second camera disposed under the machine table, wherein the second camera scans the product plate on the first fixing base synchronously with the first camera.

* * * * *